(12) United States Patent
Petraitis et al.

(10) Patent No.: US 8,188,318 B2
(45) Date of Patent: May 29, 2012

(54) METHOD OF MANUFACTURING ETHYLENEAMINES

(75) Inventors: David M. Petraitis, Covington, LA (US); Stephen W. King, League City, TX (US); Thomas Z. Srnak, Arlington Heights, IL (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 281 days.

(21) Appl. No.: 12/587,350

(22) Filed: Oct. 6, 2009

(65) Prior Publication Data

US 2010/0087681 A1    Apr. 8, 2010

Related U.S. Application Data

(60) Provisional application No. 61/195,454, filed on Oct. 6, 2008.

(51) Int. Cl.
*C07C 209/00*    (2006.01)
(52) U.S. Cl. ...................................................... 564/470
(58) Field of Classification Search .................... 564/470
See application file for complete search history.

(56) References Cited

U.S. PATENT DOCUMENTS

| | | |
|---|---|---|
| 2,861,995 A | 11/1958 | Mackenzie |
| 3,110,732 A | 11/1963 | Speranza et al. |
| 3,658,692 A | 4/1972 | Gilbert et al. |
| 3,847,754 A | 11/1974 | Oliver |
| 4,073,750 A | 2/1978 | Yates et al. |
| 4,111,840 A | 9/1978 | Best |
| 4,123,462 A | 10/1978 | Best |
| 4,209,424 A | 6/1980 | LeGoff et al. |
| 4,264,776 A | 4/1981 | Hershman et al. |
| 4,328,370 A | 5/1982 | Fazio |
| 4,400,539 A | 8/1983 | Gibson et al. |
| 4,404,405 A | 9/1983 | Winters |
| 4,510,263 A | 4/1985 | Pereira et al. |
| 4,552,961 A | 11/1985 | Herdle |
| 4,568,746 A | 2/1986 | Cowherd, III |
| 4,584,405 A | 4/1986 | Vanderpool |
| 4,602,091 A | 7/1986 | Brennan |
| 4,708,945 A | 11/1987 | Murrell et al. |
| 4,729,981 A | 3/1988 | Kobylinski et al. |
| 4,801,573 A | 1/1989 | Eri et al. |
| 4,806,517 A | 2/1989 | Vanderpool et al. |
| 4,845,296 A | 7/1989 | Ahmed et al. |
| 4,870,044 A | 9/1989 | Kukes et al. |
| 4,883,826 A | 11/1989 | Marugg et al. |
| 4,888,316 A | 12/1989 | Gardner et al. |
| 4,906,782 A | 3/1990 | Hara et al. |
| 4,922,024 A | 5/1990 | Bowman et al. |
| 4,927,931 A | 5/1990 | Molzahn et al. |
| 4,983,735 A | 1/1991 | Hartwell et al. |
| 5,030,740 A | 7/1991 | Bowman et al. |
| 5,073,635 A | 12/1991 | Bowman et al. |
| 5,120,815 A | 6/1992 | Marugg et al. |
| 5,166,442 A * | 11/1992 | Hartwell et al. ............ 564/470 |
| 5,225,599 A | 7/1993 | King et al. |
| 5,225,600 A | 7/1993 | King et al. |
| 5,248,827 A | 9/1993 | Hara et al. |
| 5,256,786 A | 10/1993 | Bowman et al. |
| 5,288,909 A * | 2/1994 | Hartwell et al. ............ 564/470 |
| 5,321,160 A | 6/1994 | Hironaka et al. |
| 5,352,835 A | 10/1994 | Dai et al. |
| 5,410,087 A * | 4/1995 | Hartwell et al. ............ 564/470 |
| H1447 H | 6/1995 | Linton |
| 5,455,352 A | 10/1995 | Huellmann et al. |
| 5,552,363 A | 9/1996 | Pannell et al. |
| 5,554,793 A * | 9/1996 | Hartwell et al. ............ 564/470 |
| 5,721,305 A | 2/1998 | Eshuis et al. |
| 5,750,790 A | 5/1998 | King |
| 5,851,948 A | 12/1998 | Chuang et al. |
| 5,935,889 A | 8/1999 | Murrell et al. |
| 6,117,814 A | 9/2000 | Plecha et al. |
| 6,124,367 A | 9/2000 | Plecha et al. |
| 6,169,207 B1 | 1/2001 | Tsuneki et al. |
| 6,222,008 B1 | 4/2001 | Gelles |
| 6,235,677 B1 | 5/2001 | Manzer et al. |
| 6,306,795 B1 | 10/2001 | Ryan et al. |
| 6,465,530 B2 | 10/2002 | Roy-Auberger et al. |
| 6,469,214 B2 | 10/2002 | Melder et al. |
| 6,534,441 B1 | 3/2003 | Bartley et al. |
| 6,576,796 B1 * | 6/2003 | Funke et al. ............ 564/470 |
| 6,703,343 B2 | 3/2004 | Park |
| 6,977,273 B2 | 12/2005 | Roy-Auberger et al. |
| 7,045,485 B2 | 5/2006 | Kelkar et al. |
| 7,053,246 B2 | 5/2006 | Gerlach et al. |

(Continued)

FOREIGN PATENT DOCUMENTS

EP    0075940    4/1983

(Continued)

OTHER PUBLICATIONS

PCT International Search Report for PCT/US2009/005469, pp. 1-5 (2010). PCT International Search Report for PCT/US2009/005473, pp. 1-4 (2010).
PCT International Search Report for PCT/US2009/005476, pp. 1-4 (2010).
PCT International Search Report for PCT/US2009/005472, pp. 1-4 (2010).
PCT International Search Report for PCT/US2009/005480, pp. 1-5 (2010).
PCT International Search Report for PCTIUS2009/005471, pp. 1-4 (2010).
PCT International Search Report for PCT/US2009/005477, pp. 1-6 (2010).
PCT International Search Report for PCT/US2009/005470, pp. 1-4 (2010).
Kiebich et al., Abstract, "Solvothermal synthesis of [C6H17N3] Sb10S16: A new thioantimonate(III) with an in-situ formed organic mine cation" (2005).

(Continued)

*Primary Examiner* — Brian J Davis
(74) *Attorney, Agent, or Firm* — Kagan Binder, PLLC

(57) ABSTRACT

The present invention provides methods of manufacturing ethyleneamines that makes use of an ethyleneamine-generating process that is coupled to a transamination process. The combination of an ethyleneamine-generating process with a transamination process improves the mix flexibility that can be obtained from the single process allowing the production of ethyleneamine compositions having an improved and more desirable product mix.

20 Claims, 11 Drawing Sheets

U.S. PATENT DOCUMENTS

| | | | |
|---|---|---|---|
| 7,053,247 | B2 | 5/2006 | Lif et al. |
| 7,056,857 | B2 | 6/2006 | Srinivasan et al. |
| 7,067,455 | B2 | 6/2006 | Chen et al. |
| 7,256,154 | B2 | 8/2007 | Moon et al. |
| 7,323,100 | B2 | 1/2008 | Espinoza et al. |
| 7,341,976 | B2 | 3/2008 | Espinoza et al. |
| 7,348,293 | B2 | 3/2008 | Timken |
| 7,393,978 | B2 | 7/2008 | Frauenkron et al. |
| 7,541,310 | B2 | 6/2009 | Espinoza et al. |
| 7,595,276 | B2 | 9/2009 | Kodama et al. |
| 7,745,369 | B2 | 6/2010 | Bhan et al. |
| 7,824,656 | B2 | 11/2010 | Idem et al. |
| 7,981,836 | B2 | 7/2011 | Kanazirev et al. |
| 2003/0013873 | A1 | 1/2003 | Neumann et al. |
| 2005/0095189 | A1 | 5/2005 | Brey et al. |
| 2006/0030726 | A1 | 2/2006 | Telschow |
| 2007/0100144 | A1 | 5/2007 | Frauenkron et al. |
| 2008/0003131 | A1 | 1/2008 | Bauer et al. |
| 2010/0056366 | A1 | 3/2010 | Lee |
| 2010/0087682 | A1 | 4/2010 | King et al. |
| 2010/0087683 | A1 | 4/2010 | Cook et al. |
| 2010/0087684 | A1 | 4/2010 | Do et al. |
| 2010/0087685 | A1 | 4/2010 | King et al. |
| 2010/0094007 | A1 | 4/2010 | King et al. |
| 2010/1008768 | | 4/2010 | King et al. |
| 2010/0137642 | A1 | 6/2010 | King et al. |

FOREIGN PATENT DOCUMENTS

| | | |
|---|---|---|
| EP | 0163253 | 12/1985 |
| EP | 0197611 | 10/1986 |
| EP | 0197612 | 10/1986 |
| EP | 0254335 | 1/1988 |
| EP | 0284398 | 9/1988 |
| EP | 0526851 | 2/1993 |
| EP | 0737669 | 10/1996 |
| EP | 1211238 | 6/2002 |
| EP | 1249440 | 10/2002 |
| EP | 1270543 | 1/2003 |
| GB | 1508460 | 4/1978 |
| IL | 57019 | 9/1983 |
| RU | 2186761 | 8/2002 |
| RU | 2226188 | 3/2004 |
| RU | 2226189 | 3/2004 |
| WO | 99/24389 | 5/1999 |
| WO | 01/44150 | 6/2001 |
| WO | 01/66247 | 9/2001 |
| WO | 01/98243 | 12/2001 |
| WO | 03/010125 | 2/2003 |
| WO | 2005/012223 | 2/2005 |
| WO | 2005/014523 | 2/2005 |
| WO | 2005/061430 | 7/2005 |
| WO | 2006/053342 | 5/2006 |
| WO | 2006/060206 | 6/2006 |
| WO | 2006/114417 | 11/2006 |
| WO | 2007/093514 | 8/2007 |
| WO | 2008/104582 | 9/2008 |
| WO | 2009/083580 | 7/2009 |

OTHER PUBLICATIONS

Komiyama et al., "Concentration Profiles in Impregnation of Porous Catalysts: Nickel on Alumina", Journal of Catalysis, vol. 63, School of Chemical Engineering, Cornell University, and Chevron Research Company, pp. 35-52 (1979).

Lewi, Abstract, Database Beilstein (online), Beilstein Institute for Organic Chemistry, Doklady Akademii Nauk SSSR, vol. 78, pp. 725-727 (1951).

Reichle, "Reactions of Aliphatic $\alpha$-$\omega$-Diamines in $H^+$-Pentasils", Journal of Catalysis, vol. 144, Union Carbide Chemicals and Plastics Company, Inc., Specialty Chemicals Division, pp. 556-568 (1993).

Tanabe et al., "A New Hypothesis Regarding the Surface Acidity of Binary Metal Oxides", Bulletin of the Chemical Society of Japan, vol. 47, Department of Chemistry, Faculty of Science, Hokkaido University, pp. 1064-1066 (1074).

Zagidullin, Abstract, "Simultaneous manufacture of acyclic and cyclic di- and polyethylenepolyamines" (1987).

* cited by examiner

US 8,188,318 B2

METHOD OF MANUFACTURING ETHYLENEAMINES

CROSS-REFERENCE TO RELATED APPLICATIONS

This application claims the benefit of United States Provisional Patent Application having Ser. No. 61/195,454 (filed on Oct. 6, 2008) and entitled METHOD OF MANUFACTURING ETHYLENEAMINES, the disclosure of which is incorporated herein by reference.

BACKGROUND

Numerous processes for the production of ethyleneamines are known. Of these processes, the two most commonly used process are (1) the reaction of ethylene dichloride (EDC) with ammonia ($NH_3$) followed by neutralization with sodium hydroxide (NaOH) to produce ethyleneamines and salt (referred to herein as "EDC Process"); and (2) the reductive amination of monoethanolamine (MEA) with ammonia ($NH_3$) over a heterogeneous catalyst (referred to herein as "RA Process"). A third viable technology, which is not commonly practiced in the industry for the production of ethyleneamines, is condensation. A condensation reaction is a chemical reaction in which two molecules (groups) combine to form a single molecule together with a loss of a small molecule (e.g., water or ammonia).

The EDC process typically produces a full range of ethyleneamines whereas the RA process is highly selective in the production of lighter amines, for example, ethylenediamine and diethylenetriamine. The condensation process typically produces a product mix that is somewhere between an EDC process and an RA processes. For each of these technologies, the degree of mix flexibility attainable is constrained by the chemistry, the process employed and the investment required to operate over a broad range of reaction conditions and the capital investment and operating costs required to recycle materials to the reactor.

In view of the limitations inherent in known ethyleneamine-generating processes, it would be desirable to have available a method of manufacturing ethyleneamines that is capable of providing an ethyleneamine manufacturer with improved product mix flexibility, and that could be cost-effectively retrofitted into an existing ethyleneamines-generating process or designed into a new plant.

SUMMARY

The present invention provides methods of manufacturing ethyleneamines that makes use of an ethyleneamine-generating process that is coupled to a transamination process. The combination of an ethyleneamine-generating process with a transamination process improves the mix flexibility that can be obtained from the single process allowing the production of ethyleneamine compositions having a controllably different and more desirable product mix. More specifically, a relatively less desirable ethyleneamine product mix (e.g., coming from a relatively less controllable ethyleneamines-generating process such as reductive amination) can be transformed into a more desirable ethyleneamine product mix by subjecting the less desirable ethyleneamines product mix to a transamination process.

In many embodiments, the method comprises the steps of: (a) manufacturing an ethyleneamines composition comprising one or more ethyleneamines using an ethyleneamine-generating process; and (b) transaminating at least a portion of the ethyleneamines composition to form a transaminated ethyleneamines composition. The transaminated ethyleneamines composition comprises at least one ethyleneamine that is present in an amount that is greater than the amount that the at least one ethyleneamine is present in the ethyleneamines composition that is transaminated in step (b). In this way, the composition of the product is increased in one or more desirable ethyleneamines (e.g., DETA, AEP and TETA) as compared to the composition that is transaminated in step (b).

DETAILED DESCRIPTION

Figure 1:
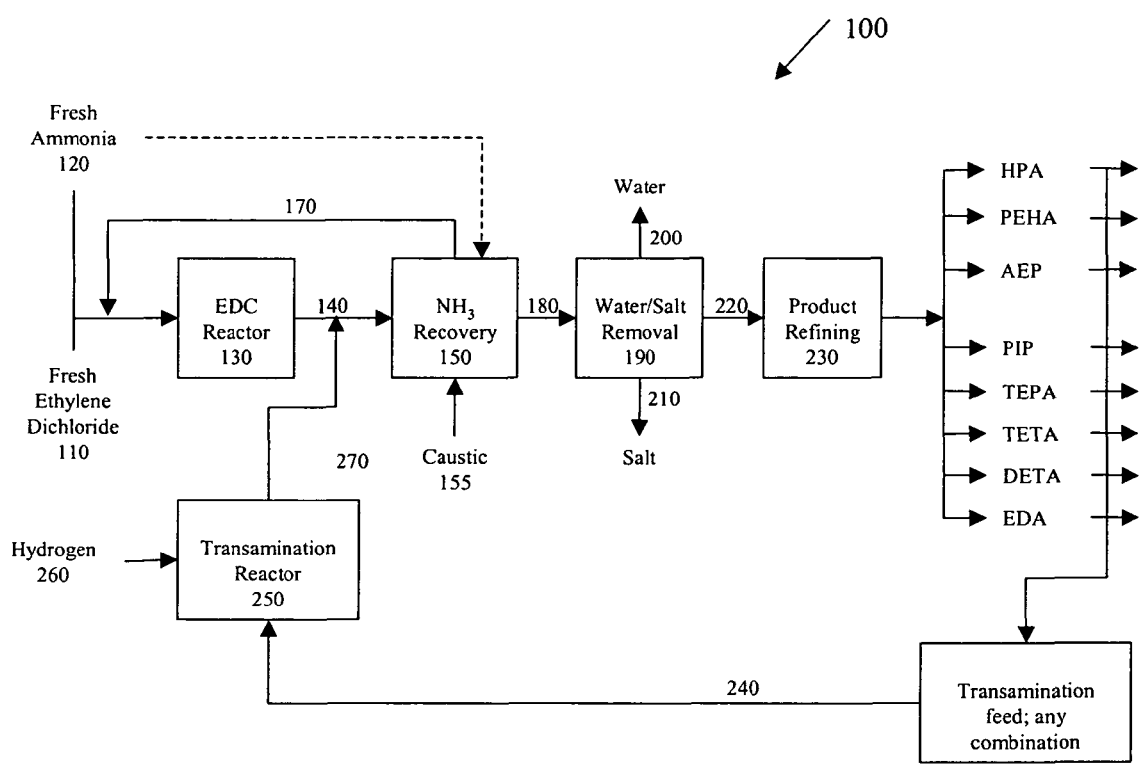
FIG. 1 is a flow chart of an embodiment of an ethyleneamines manufacturing process in accordance with the present invention.

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

All publications and patents mentioned herein are incorporated herein by reference in their respective entireties for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventor is not entitled to antedate such disclosure by virtue of prior invention.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

As used herein, the following abbreviations have the following meanings:
AEEA refers to aminoethylethanolamine.
AEP refers to aminoethylpiperazine.
DETA refers to diethylenetriamine.
EDA refers to ethylenediamine.
EDC refers to ethylenedichloride.
HEP refers to hydroxyethylpiperazine.
HPA refers to heavy polyamine.
MEA refers to monoethanolamine.
PEHA refers to pentaethylenehexamine.
PIP refers to piperazine.
TEPA refers to tetraethylenepentamine.
TETA refers to triethylenetetramine.

The present invention provides a method of making ethyleneamines that makes use of an ethyleneamine-generating process that is coupled to a transamination process. The combination of the ethyleneamine-generating process with the transamination process improves the product mix flexibility that results from the single process thereby allowing the production of ethyleneamine compositions that have an improved mix of products.

The method of the present invention includes a step of manufacturing an ethyleneamines composition using an ethyleneamine-generating process. Any process that is useful for generating ethyleneamines may be used in accordance with the present invention. Of the numerous processes known for the production of ethyleneamines, the two most commonly used processes are: (1) the reaction of ethylene dichloride (EDC) with ammonia (NH$_3$) followed by neutralization with sodium hydroxide (NaOH) to produce ethyleneamines and salt (referred to herein as "EDC Process"); and (2) the reductive amination of monoethanolamine (MEA) with ammonia (NH$_3$) over a heterogeneous catalyst (referred to herein as "RA Process"). A third viable process, which is not as commonly practiced in the industry, is condensation. Condensation is a chemical reaction in which two molecules groups combine to form a single molecule together with a loss of a small molecule (e.g., water or ammonia).

Whether utilizing EDC Process, RA Process, or condensation processes, the degree of mix flexibility that can be obtained is constrained by the chemistry, the process employed, the investment required to operate over a broad range of reaction conditions, and the capital investment and operating costs required to recycle materials to the reactor. For example, an RA process mixture comprises about 70 wt. % EDA, about 10 wt. % DETA and the ability to increase DETA selectively without significantly increasing PIP, AEP, AEEA, TETA, TEPA, PEHA and/or HPA is limited by the chemistry and the process. Although an EDC process has higher degree of mix flexibility than an RA process due to the reaction chemistry, the ability to selectively increase a particular homolog without increasing undesirable homologs is also limited. The present invention addresses these limitations by providing an improved process for generating ethyleneamines wherein an ethyleneamines-generating process is combined with a transamination process to improve product mix flexibility Useful ethyleneamine-generating processes are described in more detail below.

Ethylenedichloride Process (EDC Process)

In some embodiments of the invention, the ethyleneamines are produced using an EDC process. As used herein the term "EDC process" refers to an ethylene dichloride route to producing ethyleneamines. In this route, ethylenedichloride (1,2-dichloroethane) is reacted with ammonia followed by neutralization (e.g., with NaOH) to yield a mixture of ethyleneamine species and salt.

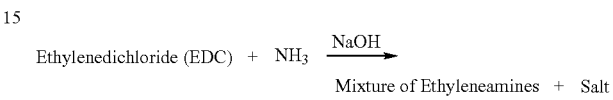

As reported in the Encyclopedia of Chemical Process and Design, in a typical process, ethylene dichloride, ammonia, and recycle liquid are combined and fed into a high pressure reactor where they react to form a mixture of ethylenediamine and polyamines. These products leave the reactor in the form of their hydrochlorides. After exiting the reactor, the unreacted ammonia can be stripped from the reactor effluent and can be recycled to the EDC reactor. After removing any excess ammonia, the ethylenediamine products are then mixed with sodium hydroxide (NaOH) to release the free amines with the resulting formation of sodium chloride. After liberation of the amines, the amine products along with sodium chloride and water can then be fed to an evaporator which crystallizes out the sodium chloride. The evaporated products can be separated, if desired, by distillation.

Using an EDC route, a typical series of reactions resulting in the formation of diethylenetriamine (DETA) is as follows:

$$2C_2H_4Cl_2+3NH_3 \rightarrow H_2NC_2H_4NHC_2H_4NH_2.4HCl$$

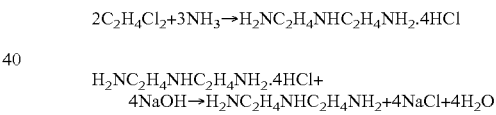

The EDC process typically produces a mixture of ethyleneamines comprising EDA, PIP, DETA, AEP, TETA, TEPA, PEHA, HPA, PEHA, TEPA, and TETA.

Useful reactor types for conducting the EDC process reaction include plug flow and tubular reactors. The reactivity of EDC and NH$_3$ is such that the reaction is auto-catalytic and catalysts are not typically used in an EDC process.

Typical reaction conditions for an EDC processes are known in the art and include, for example, heating the reactor mixture up to about 140° C. at a pressure of about 2000 psig feeding the rector.

In many embodiments, the EDC process is followed by a water and salt recovery process. Water and salt are typically removed from the process by a series of evaporators, also referred to as crystallizers, followed by conventional distillation.

Reductive Amination Process (RA Process)

In some embodiments of the invention, the ethyleneamine-generating process is a reductive amination process ("RA Process"). In reductive amination ("RA"), a feed stream comprising one or more alkanolamines (e.g., monoethanolamine, diethanolamine, and triethanolamine) is reacted with ammonia (NH$_3$) in the presence of a catalyst (e.g., a Ni—Re heterogeneous catalyst) to produce a mixture of ethyleneamines typically including ethylenediamine (EDA).

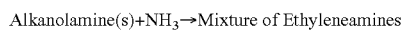

Alkanolamines include compounds that include at least one linear, branched, or cyclic alkylene chain, at least one hydroxyl group, and at least one amine moiety. In preferred embodiments, the alkylene chain has from 2 to 20, preferably 2 to 10, more preferably 2 to 5 carbon atoms. Of these, ethylene, —$CH_2CH_2$—, is preferred. Examples of ethanolamines include monoethanolamine, diethanolamine, and triethanolamine, although others may be useful.

In exemplary embodiments, the RA feed stream that is fed to the RA reactor comprises about 70 wt. % or greater monoethanolamine, about 30 wt. % or less diethanolamine, and about 15 wt. % triethanolamine or less, based on the total ethanolamines content. Typically, the sum of diethanolamine and triethanolamine is about 30 wt. % or less. In some embodiments, the RA feed stream comprise about 90 wt. % or greater monoethanolamine, about 3 wt. % or less diethanolamine, and about 0.5 wt. % or less triethanolamine. In other embodiments, the RA feed stream comprise about 99.5 wt. % or greater monoethanolamine, about 0.3 wt. % or less diethanolamine, and less than about 0.1 wt. % or less triethanolamine.

The RA feed stream also contains ammonia in an amount which is typically in stoichiometric excess of the alcoholic hydroxyl groups that are present in the RA feed stream. In some embodiments, there are at least 10 moles of ammonia for each mole of ethanolamine in the RA feed stream. In other embodiment, at least 15 moles of ammonia or at least 20 moles of ammonia are present in the feed stream.

Water may also be present in the RA feed stream, for example, in an amount ranging from about 0 to 10 wt. %, more typically 0 to 5 wt. %.

In some embodiments, an amine component is also included in the feed stream for the RA process. Examples of amines include EDA, PIP, DETA, and TETA. The amine component may be introduced into the RA feed stream by way of recycling unreacted amine components.

Representative catalysts for the RA process are known in the art and include, for example, nickel rhenium type catalysts. Other transition metal catalysts such as Co, Cu, Ru, Rh, Pd, Pt, or mixtures thereof may also be useful. The catalysts are typically provided on a support, for example, an oxide support such as $Al_2O_3$, $TiO_2$, $ZrO_2$, or $SiO_2$. Also useful are zeolite catalysts such as mordenites, faujasites, and chabazites.

In particularly preferred embodiments, the catalyst material incorporates hydrogenation/de-hydrogenation catalytic ingredients comprising nickel and rhenium. The weight ratio of nickel to rhenium may vary over a wide range. For instance; the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than about 1:1. In some embodiments, using a weight ratio from about 3:1 to about 10:1 would be suitable. In preferred embodiments in which a heterogeneous catalyst incorporates nickel and rhenium, a useful support are alumina-silicate particles. Such catalysts and methods of making such heterogeneous catalysts on such supports are further described in U.S. Pat. No. 6,534,441. Also useful are the nickel and rhenium catalysts that are reported in U.S. Pat. Nos. 4,123,462 and 4,111,840.

To maintain the catalyst activity when metal catalysts are used, it is often desirable to introduce hydrogen gas into the RA reactor. The hydrogen gas may be supplied to the amination reactor as a separate feed stream or as a component of the amination feed stream. Typically, the amount of hydrogen that is present ranges from about 0.0001 to about 30 mole percent, more typically about 0.001 to about 2 mole percent based on the total moles in the amination feed stream.

The temperature of the amination reaction is selected based upon the type of catalyst used for the amination reaction. For Ni—Re, the temperature typically ranges from about 120 to about 225° C., more typically ranging from about 150 to about 215° C. The pressure typically ranges from about 1000 to about 4000 psi.

After the effluent stream is removed from the RA reactor, it can be subjected to a variety of separation steps for removing the various components. For example, the effluent stream may be subjected to distillation to remove water, ammonia, ethylenediamine, monoethanolamine, hydroxyethylpiperazine, aminoethylethanolamine, and the like.

The RA process typically produces a mixture of ethyleneamines that is high in the ethyleneamines EDA and DETA, and comprises minor amounts of HPA, PEHA, AEEA, AEP, PIP, TEPA, and TETA. For example, in some embodiments, the ethyleneamines composition comprises about 70 wt. % EDA, about 10 wt. % DETA, and about 20 wt. % total of HPA, PEHA, AEEA, AEP, PIP, TEPA, and TETA.

Condensation Process

A third viable technology, which is not commonly practiced in the industry for the production of ethyleneamines, is condensation. Generally speaking, a condensation reaction is a chemical reaction in which two molecules or functional groups combine to form one single molecule, together with the loss of a small molecule. In some embodiments, a hydroxyl containing material is reacted with an amine to produce water and a different amine. For example, the reaction of an ethanolamine with an ethyleneamine produces a new ethyleneamine with the loss of water. In some embodiments, an amine is reacted with an amine to produce ammonia and a different amine. For example, the reaction of an ethyleneamine with an ethyleneamine produces a new ethyleneamine with the loss of ammonia. Additional details regarding condensation processes can be found, for example, in U.S. Pat. No. 5,225,600 (King et al.).

For EDC, RA, and condensation processes, the degree of mix flexibility that can be obtained is constrained by the chemistry, the process employed, the investment required to operate over a broad range of reaction conditions, and the capital investment and operating costs required to recycle materials to the reactor. For example, an RA process mixture comprises about 70 wt. % EDA, about 10 wt. % DETA and the ability to increase DETA selectively without significantly increasing PIP, AEP, AEEA, TETA, TEPA, PEHA and/or HPA is limited by the chemistry and the process. Although an EDC process has higher degree of mix flexibility than an RA process due to the reaction chemistry, the ability to selectively increase a particular homolog without increasing undesirable homologs is also limited.

Ammonia/Hydrogen Recovery

One or more ammonia recovery systems can be used in the process of making ethyleneamines according to the present invention. An ammonia recovery system separates ammonia, and optionally one or more additional components (e.g., hydrogen), from a fluid stream.

An ammonia recovery system can be positioned anywhere in the overall process as desired. Preferably, one or more ammonia recovery systems are used in a manner that minimizes the number of ammonia recovery systems and/or other process units. The recovered ammonia can be used in any desired manner. For example, depending on the purity level of the recovered ammonia, the recovered ammonia may be recycled to another point in the process such as the inlet of a reactor. Advantageously, such recovered ammonia can be used as "make-up" ammonia for a reactor where ammonia is consumed in a reaction.

Ammonia recovery systems can be any type of ammonia recovery system known in the art. For example, an ammonia recovery system can utilize distillation columns, multiple single stage separators, compressors, chillers and/or absorbers in many different combinations and the like.

Separation

After producing a mixture of ethyleneamines using an ethyleneamine-generating process (e.g., EDC process, RA process, or condensation process), the resulting ethyleneamines composition may then be subjected to one or more separation steps. In the separation steps, at least a portion of at least one ethyleneamine is removed from the ethyleneamines composition to form a separated mixture. For example, the ethyleneamines EDA, DETA, HPA, PEHA, AEEA, AEP, PIP, TEPA, and TETA may be partially or fully removed from the ethyleneamines composition. The resulting separated ethyleneamines composition comprises one or more ethyleneamines. In some embodiments, the separated ethyleneamines composition comprises two or more ethyleneamines, or three or more ethyleneamines. The separation step is typically conducted using one or more known techniques for separating ethyleneamines, such as distillation (optionally using divided wall columns), membrane separation, melt crystallization, and reactive distillation.

Transamination

After generating an ethyleneamines composition, the ethyleneamines composition is then transaminated. Transamination is a transfer of an amino group from one chemical compound to another, or the transposition of an amino group within a chemical compound. The transamination results in an increase in at least one ethyleneamine as compared to the amount the at least one ethyleneamine is present in the mixture that is transaminated. In other words, the transamination causes at least one ethyleneamine that is present in the ethyleneamines composition to increase in amount as compared to the amount that the ethyleneamine is present prior to transamination. For example, in an exemplary embodiment, the transamination may increase the amount of DETA from 0 wt. % in the ethyleneamines composition that is transaminated (i.e., the transamination feed material) to 23 wt. % in the transaminated ethyleneamines composition.

Optionally, one or more additional components can be combined with the ethyleneamine reactants prior to and/or within the transamination reactor. For example ammonia ($NH_3$) can be included in the transamination feed stream to minimize the extent of unfavorable reaction(s). As another example, hydrogen can be included in the transamination feed stream in an amount sufficient to affect catalyst activity and product selectivity. Exemplary amounts of hydrogen include about 0.001 to about 10.0 mole % based on liquid feed.

The transamination reaction can be practiced in any suitable reactor. These include batch reactor, continuous fixed bed reactors, slurry bed reactors, fluidized bed reactors, catalytic distillation reactors, combinations of these, and the like. In certain embodiments, a fixed bed reactor is preferred. A fixed bed reactor includes catalyst pellets that are held in place and do not substantially move with respect to fixed reference frame. At least a portion of the reactor feed material passes over (flows past) the catalyst pellets and reacts to form product(s).

The reactor conditions can be set so as to form a desired product mix given the reactor feed and catalyst(s) used. Preferably, the reactor conditions are relatively moderate so as to reduce operating costs and the like. A preferred transamination reaction temperature can be a temperature in the range of from about 130° C. to about 180° C., preferably in the range of from about 130° C. to about 170° C., even more preferably in the range of from about 130° C. to about 160° C. A preferred transamination reaction pressure can be a pressure in the range of from about 200 to about 2000 psig. A preferred transamination reaction reactor space velocity can be in the range of from about 5 to about 50 gram moles of ethyleneamines per kilogram of catalyst per hour. In preferred embodiments, a transamination reaction according to the present invention can have feed conversions of about 25% or more, for example, in the range of from about 25% to about 65%.

Any catalyst that can catalyze a transamination reaction can be used in a process according to the present invention. Such catalysts are well known. A preferred catalyst includes a hydrogenation catalyst or dehydrogenation catalyst. A hydrogenation catalyst can be made of nickel (Ni), copper (Cu), cobalt (Co), ruthenium (Ru), rhenium (Re), rhodium (Rh), platinum (Pt), palladium (Pd), and combinations thereof. Any catalyst support that can support a catalyst for a transamination reaction can be used in a process according to the present invention. Catalyst supports are well known and include, e.g., metal oxide. In preferred embodiments, a mixed metal oxide is used, and more preferably a transitional alumina containing silica is used.

One preferred catalyst is a selective and stable catalyst that includes rhenium and nickel supported on an $Al_2O_3$—$SiO_2$ carrier. Such a catalyst is described in U.S. Pat. No. 6,534,441 (Bartley et al.). As mentioned, such a catalyst includes nickel and rhenium as active metals. More particularly, the catalyst can include from about 2 to about 75 wt. % nickel and has a nickel to rhenium wt. % ratio of from about 1:1 to about 200:1. The catalyst is preferably supported on an alumina-silica support which contains from about 5 to about 65 wt. % silica and preferably has a BET surface area of from about 30 to about 450 square meters per gram. The catalyst optionally includes boron and preferably has a boron to nickel wt. % ratio less than or equal to about 1. The nickel content of the catalyst, the nickel to rhenium and boron to nickel wt. % ratios, the support surface area, and the silica content of the support can be selected to provide the catalyst composition with a specified activity, and to provide a particular mix of amine products.

Another preferred transamination catalyst is described in U.S. Provisional Patent Application having Ser. No. 61/195, 455 and entitled "CATALYST COMPOSITIONS INCLUDING MIXED METAL OXIDE COMPLEX AS SUPPORT" (filed Oct. 6, 2008) in the names of King et. al.

In some embodiments, the transamination catalyst comprises: (a) a support portion comprising an acidic mixed metal oxide comprising a transitional alumina and a second metal oxide; and (b) a catalyst portion comprising nickel and rhenium, wherein: the second metal oxide has a weight percentage that is less than the weight percentage of alumina, the catalyst portion is 25 weight percent or less of the catalyst composition, the catalyst portion comprises nickel in an amount in the range of 2 to 20 weight percent, based upon total catalyst composition weight, and there is no boron in the catalyst portion.

In some embodiments, the transitional alumina comprises delta alumina, and may further comprise one or more of gamma, theta or alpha alumina. In some embodiments, the transitional alumina comprises theta alumina, and may further comprise one or more of gamma or alpha alumina. In some embodiments, the support portion comprises at least 50 weight percent transitional phase alumina.

In some embodiments, the second metal oxide comprises at least one element selected from Group IIA, IIIA, IVA, VA, VIA, IIB, IIIB, IVB, VB, VIB, VIIB and a rare earth element of the Periodic Table. Examples of the second metal oxide include silicon, lanthanum, magnesium, zirconium, boron, titanium, niobium, tungsten and cerium. In some embodiments, the support portion comprises the second metal oxide in an amount in the range of 5 weight percent to less than 50 weight percent, based upon the weight of the support portion, or in the range of 5 weight percent to 35 weight percent, based upon the weight of the support portion.

In some embodiments, the support portion has a surface area in the range of 10 m$^2$/g to 200 m$^2$/g, or in the range of 80 m$^2$/g to 180 m$^2$/g.

In some embodiments, the nickel and rhenium are present in the catalyst portion in a weight ratio in the range of 3:1 to 14:1.

In some embodiments, the catalyst further comprises a selectivity promoter. The selectivity promoter may comprise at least one element selected from Group IA, Group IIA, Group IIIA, except for boron, Group IVA, Group VA, Group VIA, Group VIIA, Group VIIIA, Group IB, Group IIB, and Group IVB of the Periodic Table.

Yet another preferred transamination catalyst is described in U.S. Provisional Patent Application having Ser. No. 61/195,434 and entitled "COBALT CATALYSTS FOR AMINE CONVERSION", filed Oct. 6, 2008 in the names of King et al. In some embodiments, the catalyst composition comprises (a) a support portion comprising an acidic mixed metal oxide comprising a transitional alumina and a second metal oxide, wherein the second metal oxide has a weight percentage that is less than the weight percentage of alumina; and (b) a catalyst portion comprising one or more metals selected from the group consisting of cobalt, nickel, and copper, wherein there is no, or less than 0.01 wt. % rhenium in the catalyst composition, and the catalyst portion is 25 wt. % or less of the catalyst composition.

In some embodiments, the catalyst portion is 20 wt. % or less of the catalyst composition, for example, in the range of 3 wt. % to 18 wt. % or in the range of 5 wt. % to 10 wt. % of the catalyst composition.

In some embodiments, the catalyst portion comprises two or three metals selected from the group consisting of cobalt, nickel, and copper, for example, cobalt and nickel.

In some embodiments, the cobalt and nickel are present in a weight ratio in the range of 1:9 to 9:1, or in the range of 1:4 to 4:1. In some embodiments, the catalyst portion comprises no rhenium, or less than 0.005 wt. % rhenium.

In some embodiments, the catalyst composition further comprises a selectivity promoter. Examples of selectivity promoter include at least one element selected from Group IA, Group IIA, Group IIIA, Group IVA, Group VA, Group VIA, Group VIIA, Group VIIIA, Group IB, Group IIB, and Group IVB of the Periodic Table. The selectivity promoter is not rhenium, rhodium, platinum, palladium, or iridium.

In some embodiments, the transitional alumina comprises delta alumina, and may further comprise one or more of gamma, theta or alpha alumina. In some embodiments, the transitional alumina comprises theta alumina, and may further comprise one or more of gamma or alpha alumina. The support portion may comprise at least 50 weight percent transitional phase alumina.

In some embodiments, the second metal oxide comprises at least one element selected from Group IIA, IIIA, IVA, VA, VIA, IIB, IIIB, IVB, VB, VIB, VIIB and a rare earth element of the Periodic Table. Examples include silicon, lanthanum, magnesium, zirconium, boron, titanium, niobium, tungsten and cerium.

In some embodiments, the support portion comprises the second metal oxide in an amount in the range of 5 weight percent to less than 50 weight percent, or in an amount in the range of 5 weight percent to 35 weight percent, based upon the weight of the support portion.

In some embodiments, the support portion has a surface area in the range of 10 m$^2$/g to 200 m$^2$/g, or in the range of 80 m$^2$/g to 180 m$^2$/g.

Embodiments of the above-described catalysts show significantly improved selectivity to ethylenediamine. Advantageously, such catalyst can achieve much improved selectivity at relatively moderate temperature and pressure conditions. For example, such catalyst can achieve the desired product selectivity at a temperature in the range of from 110° C. to 180° C., preferably from 130° C. to 160° C., and a pressure of 2000 psig or less.

After transamination, the transamination reactor effluent may be either returned to a common separations system for recovery, recovered via a separate refining system, or any combination of shared separation schemes.

The one or more ethyleneamines made by a process according to the present invention can be separated (refined) by any method known in the art. For example, the ethyleneamines can be refined using conventional distillation technology known in the art. Preferably, dividing wall columns are used. Other separation techniques such as membrane separation, melt crystallization, and reactive distillation may also be employed.

The transamination process can be configured as a stand-alone unit (i.e., not integrated with a new or existing ethyleneamines facility) or it may be partially-integrated or fully-integrated with a new or existing ethyleneamines facility. Examples of stand-alone transamination processes are described in U.S. Provisional Patent Application having Ser. No. 61/195,404 and entitled "A PROCESS TO SELECTIVELY MANUFACTURE DIETHYLENETRIAMINE (DETA) AND OTHER DESIRABLE ETHYLENEAMINES VIA CONTINUOUS TRANSAMINATION OF ETHYLENEDIAMINE (EDA), AND OTHER ETHYLENEAMINES OVER A HETEROGENEOUS CATALYST SYSTEM", filed Oct. 6, 2008 in the name of Cook et al. In a fully-integrated embodiment, the transamination reactor makes use of ammonia recovery and product refining operations from the ethyleneamine-generating process. In a partially-integrated embodiment, at least one process or unit operation in the ethyleneamine generating process is used to recover materials from the transamination reactor effluent. For example, in a partially-integrated embodiment, the transamination reactor may be connected to an ammonia recovery unit that is separate from the ammonia recovery unit that treats the products of the ethyleneamine-generating process.

The product of the transamination reaction includes an ethyleneamines composition that is enriched in one or more desirable ethyleneamines as compared to the ethyleneamines composition that is subjected to the transamination. For example, in some embodiments, the amount of TETA that is present in the transaminated ethyleneamines composition is enriched as compared to the ethyleneamines composition that is transaminated. For example, the amount of TETA in the transaminated ethyleneamines composition may range from about 0 wt. % to about 75 wt. %, preferably 0 wt % to 50 wt %, more preferably 0 wt % to 20 wt %. In other embodiments, the amount of DETA that is present in transaminated ethyleneamines composition is enriched as compared to the ethyleneamines composition that is transaminated. For example, the amount of DETA in the transaminated ethyleneamines composition may range from about 0 wt. % to about 99 wt. %, preferably 0% to 80%, more preferably 0% to 50%. In yet other embodiments, the amount of EDA that is present in transaminated ethyleneamines composition is enriched as compared to the ethyleneamines composition that is transaminated. For example, the amount of EDA in the transaminated ethyleneamines composition may range from about 0 wt. % to about 75 wt. %, preferably 0 wt % to 50 wt %, more preferably 0 wt % to 20 wt %. In yet other embodiments, the amount of AEP that is present in transaminated ethyleneamines composition is enriched as compared to the ethyleneamines composition that is transaminated. For example, the amount of AEP in the transaminated ethyleneamine composition may range from about 0 wt. % to about 75 wt. %, preferably 0 wt % to 50 wt %, more preferably 0 wt % to 20 wt %.

Process Flow Diagrams

The invention will now be described with reference to the following exemplary process flow diagrams. Referring now to FIG. 1, a process flow diagram of an embodiment of a process of the invention is shown.

A fully-integrated process 100 of the present invention using an EDC reactor is shown in FIG. 1. As shown in FIG. 1, a feed of fresh ethylene dichloride 110 is fed along with fresh ammonia 120 into EDC reactor 130. The product stream 140 of the EDC reaction is then fed into an ammonia recovery process 150 where the reactor effluent is neutralized with caustic 155, and unreacted ammonia from the reaction is removed from the products 140 by methods known in the art (e.g., conventional distillation). The unreacted ammonia is then fed back to EDC reactor 130 through recycle stream 170. Optionally, the fresh ammonia 120 fed to the EDC reactor 130 may be introduced into the ammonia recovery process 150 and recycled back to the EDC reactor 130 by stream 170. After ammonia recovery 150, the product stream 180 is then fed into a water/salt removal process 190 where water 200 and salt 210 are removed using methods known in the art (e.g., evaporation and crystallization followed by conventional distillation). After the water and salt have been removed, the product stream 220 is then fed into a product refining step 230 where the various ethyleneamines that are present in the product stream can be separated from one another or in fractions. The product refining step typically comprises conventional distillation, preferably a combination of conventional and dividing wall columns. After the refining step 230, a stream 240 comprising one or more ethyleneamines are then fed into a transamination reactor 250. Transamination reactor 250 is also fed with hydrogen stream 260. The transamination product 270 is then fed into the ammonia recovery process 150 for processing along with the EDC product stream 140. Hydrogen contained in stream 270 may be vented from ammonia recovery process 150 or it may be recycled to the EDC reactor 130 by stream 170 where it will be consumed.

Figure 1A:
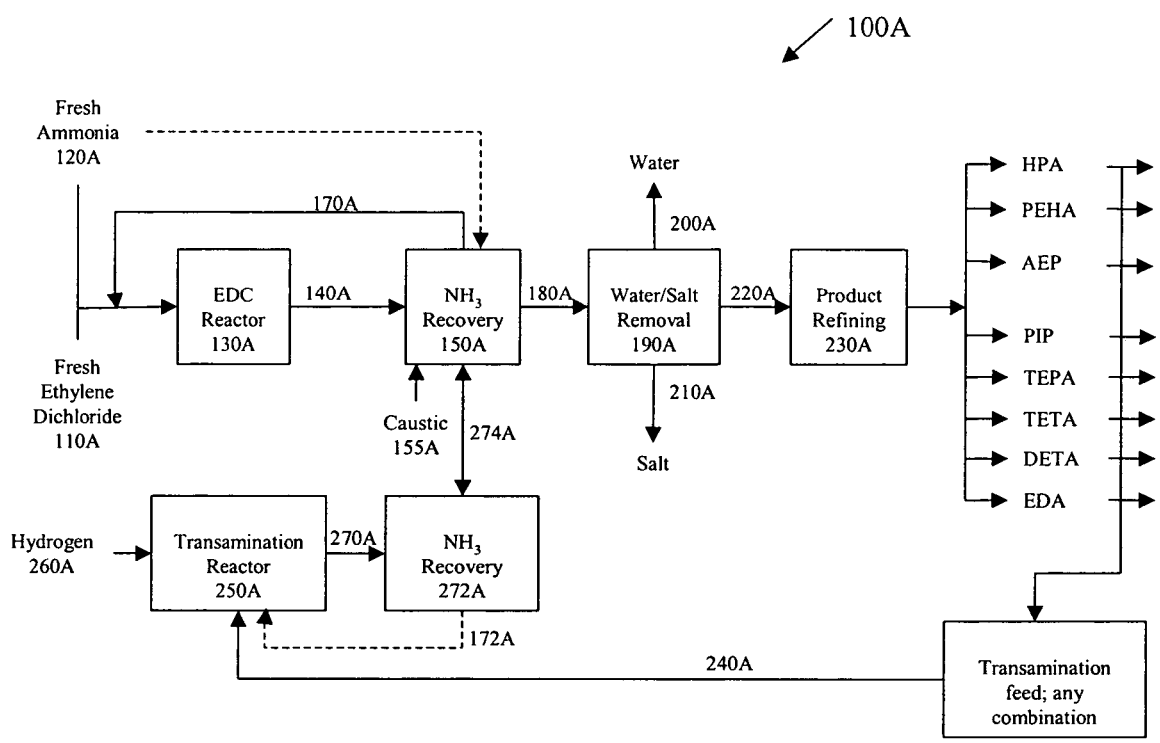
FIG. 1A is a flow chart of an embodiment of an ethyleneamines manufacturing process in accordance with the present invention.

Referring now to FIG. 1A, a process flow chart of an embodiment of a process of the invention is shown. The process shown in FIG. 1A is representative of a partially-integrated process. Process 100A may be useful for adapting an existing EDC line to perform the process of the present invention. Process 100A includes primary ammonia recover unit 150A and secondary ammonia recovery unit 272A in series or parallel with one another. In the process of FIG. 1A, the transamination products 270A from transamination reactor 250A are fed into secondary ammonia recovery unit 272A. Secondary ammonia recovery unit 272A provides additional ammonia recovery capacity for process 100A. Secondary ammonia recovery unit 272A and ammonia recovery unit 150A are integrated in such a manner that materials from either unit can move via stream 274A, as required. Stream 274A may actually be multiple lines going between the two ammonia recovery units 150A and 272A. Hydrogen contained in stream 274A is either vented from unit 150A or recycled to the EDC reactor via stream 170A where it will be consumed. Optionally, a hydrogen containing stream 172A can be recovered in the secondary ammonia recovery unit 272A and recycled to the transamination reactor 250A. After ammonia recovery 272A, the product stream 274A is then fed into primary ammonia recovery unit 150A for further downstream processing.

Figure 1B:
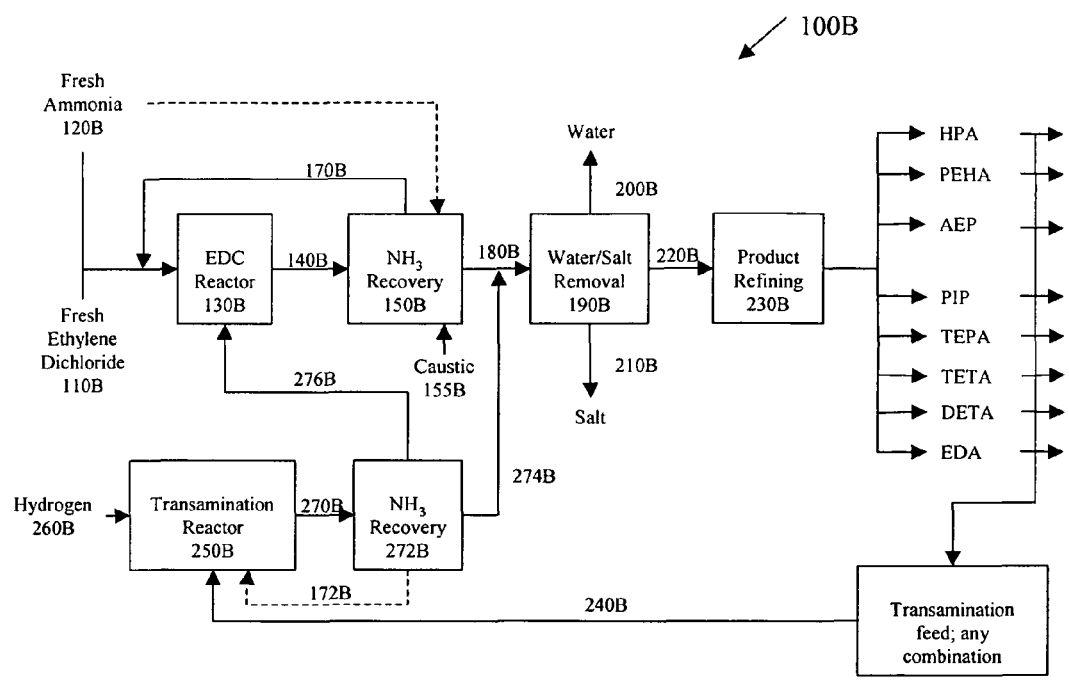
FIG. 1B is a flow chart of an embodiment of an ethyleneamines manufacturing process in accordance with the present invention.

Referring now to FIG. 1B, a process flow chart of an embodiment of a process of the invention is shown. The process shown in FIG. 1B is representative of a partially-integrated process. Process 100B may be useful for adapting an existing EDC line to perform the process of the present invention. Process 100B includes primary ammonia recover unit 150B and secondary ammonia recovery unit 272B that are integrated in a parallel relationship. In the process of FIG. 1B, the transamination products 270B from transamination reactor 250B are fed into secondary ammonia recovery unit 272B. Secondary ammonia recovery unit 272B provides additional ammonia recovery capacity for process 100B. After ammonia recovery, the product stream 274B is then fed back into product stream 180B after primary ammonia recovery unit 150B. Recovered ammonia 276B is recycled back into EDC reactor 130B. Hydrogen contained in stream 276B will either be consumed in EDC reactor 130B or vented from ammonia recover unit 150B. Optionally, a hydrogen containing stream 172B may be recovered in the secondary ammonia recovery unit 272B and recycled to the transamination reactor 250B.

Figure 1C:
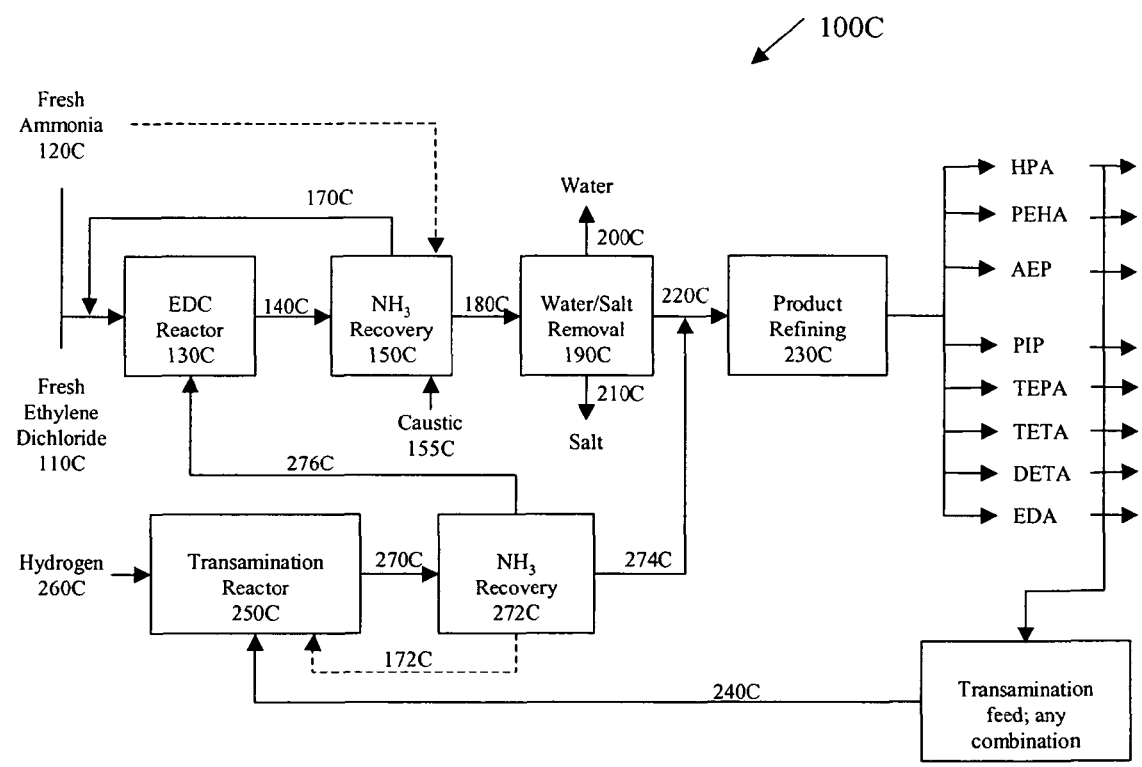
FIG. 1C is a flow chart of an embodiment of an ethyleneamines manufacturing process in accordance with the present invention.

Referring now to FIG. 1C, a process flow chart of an embodiment of a process of the invention is shown. The process shown in FIG. 1C is representative of a partially-integrated process. Process 100C may be useful for adapting an existing EDC line to perform the process of the present invention. Process 100C includes primary ammonia recovery unit 150C and secondary ammonia recovery unit 272C that are in a parallel relationship. In the process of FIG. 1C, the transamination products 270C from transamination reactor 250C are fed into secondary ammonia recovery unit 272C. Secondary ammonia recovery unit 272C provides additional ammonia recovery capacity for process 100C. After ammonia recovery, the product stream 274C is then fed back into product stream 220C after water/salt removal process 190C. Recovered ammonia 276C is recycled back into EDC reactor 130C. Hydrogen contained in stream 276C will either be consumed in EDC reactor 130C or vented from ammonia recovery unit 150C. Optionally, a hydrogen containing stream 172C can be recovered in the secondary ammonia recovery unit 272C and recycled to the transamination reactor 250C.

Figure 1D:
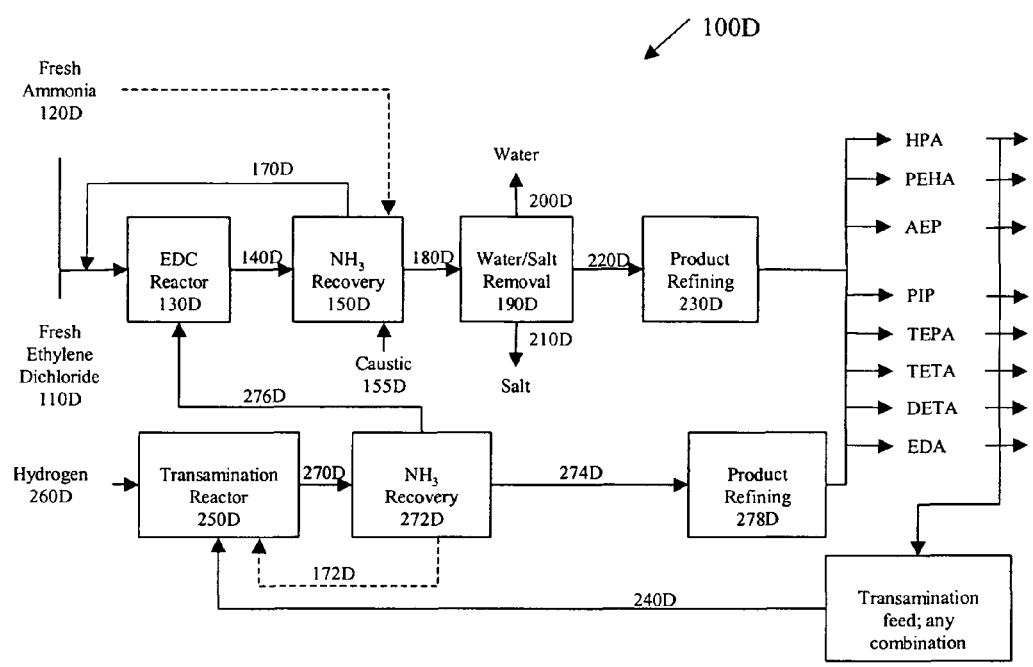
FIG. 1D is a flow chart of an embodiment of an ethyleneamines manufacturing process in accordance with the present invention.

Referring now to FIG. 1D, a process flow chart of an embodiment of a process of the invention is shown. The process shown in FIG. 1D is representative of a partially-integrated process. Process 100D may be useful for adapting an existing EDC line to perform the process of the present invention. Process 100D includes separate ammonia recovery and product refining streams for the EDC reactor 130D and transamination reactor 250D. As shown in FIG. 1D, the product 270D of transamination reactor 250D is fed into ammonia recovery unit 272D. The product stream 274D from the ammonia recovery unit is then fed into product refining unit 278D. The recovered ammonia 276D is recycled back into EDC reactor 130D. Hydrogen contained in stream 276D will either be consumed in EDC reactor 130D or vented from ammonia recovery unit 150D. Optionally, a hydrogen containing stream 172D can be recovered in the secondary ammonia recovery unit 272D and recycled to the transamination reactor 250D. The product refining unit 278D may be the same or different than product refining unit 230D that is used to treat the EDC stream.

Figure 1E:
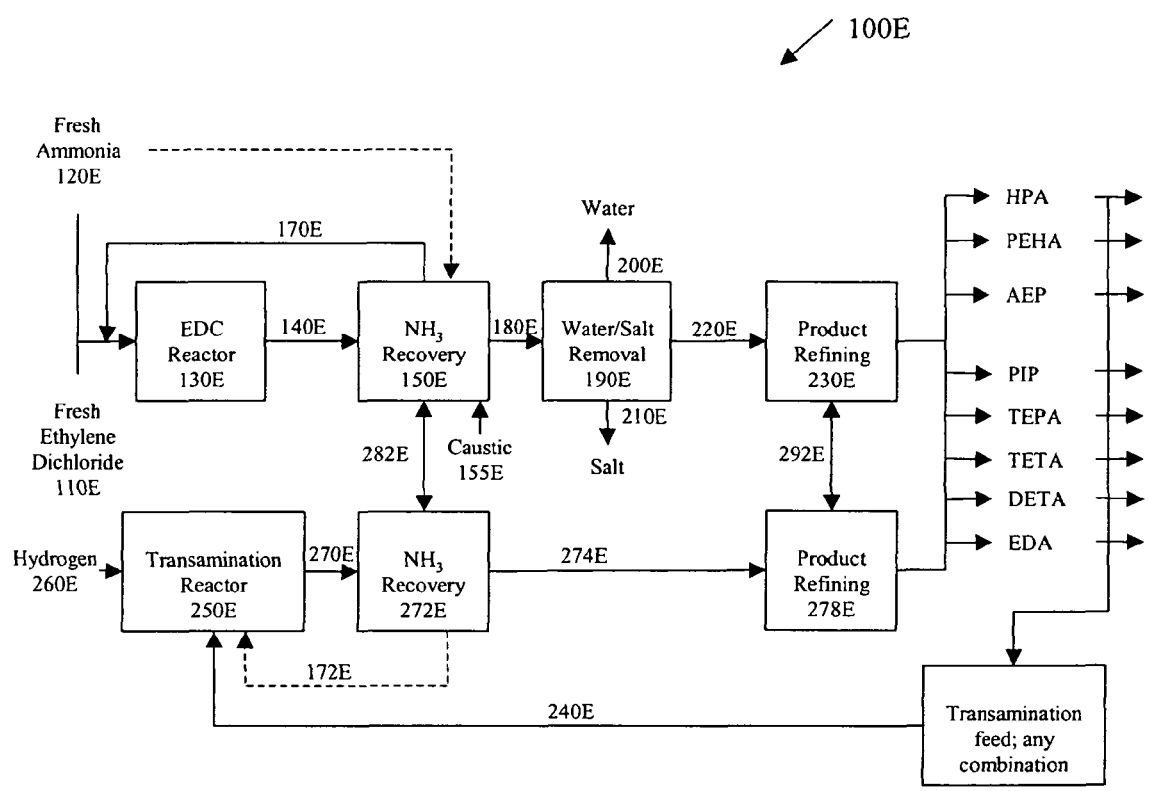
FIG. 1E is a flow chart of an embodiment of an ethyleneamines manufacturing process in accordance with the present invention.

Referring now to FIG. 1E, a process flow chart of an embodiment of a process of the invention is shown. The process shown in FIG. 1E is representative of a partially-integrated process. Process 100E may be useful for adapting an existing EDC line to perform the process of the present invention. Process 100E includes fully or partially-integrated ammonia recovery and product refining streams for the EDC reactor 130E and transamination reactor 250E. As shown in FIG. 1E, the product 270E of transamination reactor 250E is fed into ammonia recovery unit 272E. The product stream 274E from the ammonia recovery unit 272E is then fed into product refining unit 278E. Ammonia recovery units 150E and 272E are coupled by stream 282E. This allows product from the EDC reactor 130E or transamination reactor 250E to be directed into the other unit for processing. Product refining units 230E and 278E are coupled by stream 292E. This allows product from either refining unit to be directed into the other refining unit for processing. Streams 282E and 292E are a depiction of the ability to transfer materials between systems. Due to the number of possible equipment combinations, 282E and 292E may actually be multiple flows going between the two systems. The product refining unit 278E may be the same or different than product refining unit 230E that is used to treat the EDC product stream.

Figure 2:
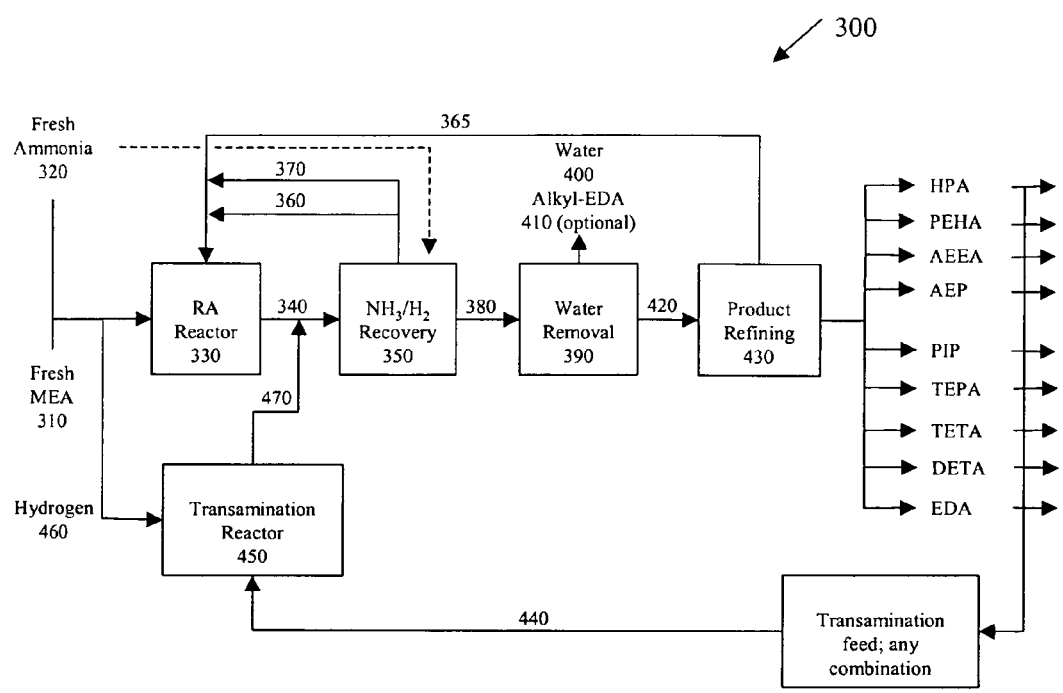
FIG. 2 is a flow chart of an embodiment of an ethyleneamines manufacturing process in accordance with the present invention.

Referring now to FIG. 2, a process flow chart of an embodiment of a process of the invention using RA is shown. A process 300 of the present invention using an RA reactor is shown in FIG. 2. As shown in FIG. 2, a feed of fresh MEA 310 and a feed of fresh ammonia 320 are fed into RA reactor 330. The product stream 340 of the RA reaction is then fed into a hydrogen and ammonia recovery process 350 where unreacted hydrogen and ammonia is removed from the product stream 340, typically via conventional distillation. The recovered ammonia is then recycled to RA reactor 330 through recycle stream 360. The recovered hydrogen is then recycled back into RA reactor 330 through recycle stream 370. Optionally, the hydrogen and ammonia may be recycled back to the RA reactor 330 as one stream. Optionally, the fresh ammonia 320 normally fed to the RA reactor 330 can be introduced into the ammonia recovery process 350 and recycled back to the RA reactor 330 via stream 360. After ammonia/hydrogen recovery 350, the product stream 380 is then fed into a water removal process 390 where water 400 and alkyl-EDA 410 (optional) are removed. The alkyl-EDA water removal step may be conducted, for example, as described in U.S. Provisional Patent Application having Ser. No. 61/195,405 and entitled "METHODS FOR MAKING ETHANOLAMINE(S) AND ETHYLENEAMINE(S) FROM ETHYLENE OXIDE AND AMMONIA, AND RELATED METHODS", filed Oct. 6, 2008 in the names of Do et. al. Optionally, the alkyl-EDA 410 does not have to be removed at this point and may be allowed to pass through in product stream 420 and recovered with the EDA product in the product refining step 430. After the water and optionally alkyl-EDA have been removed, the product stream 420 is then fed into a product refining step 430 where the various ethyleneamines that are present in the product stream can be separated from one another or into various fractions. Unreacted MEA is recovered in the product refining step 430 and recycled to the RA reactor via stream 365. The product refining step 430 typically comprises conventional distillation process, optionally including divided wall columns. After the refining step 430, the product stream 440 comprising one or more ethyleneamines are then fed into a transamination reactor 450. Transamination reactor 450 is fed with a hydrogen stream 460 which also feeds RA reactor 330. As shown in FIG. 2, the transamination products 470 are fed into RA product stream 340 prior to the ammonia/hydrogen recovery 350.

Figure 2A:
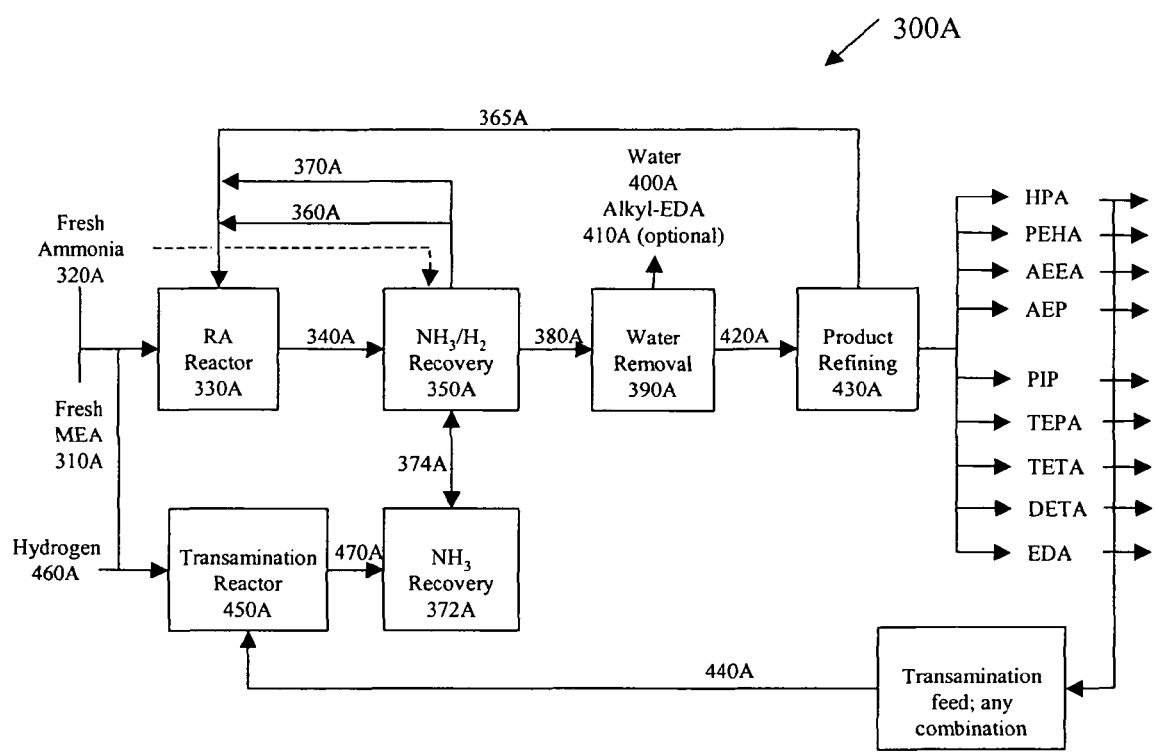
FIG. 2A is a flow chart of an embodiment of an ethyleneamines manufacturing process in accordance with the present invention.

Referring now to FIG. 2A, a process flow chart of an embodiment of a process of the invention using RA is shown. The process shown in FIG. 2A is representative of a partially-integrated process. Process 300A may be useful for adapting an existing RA line to make use of the process of the present invention. Process 300A includes primary ammonia/hydrogen recovery unit 350A and secondary ammonia recovery unit 372A. In the process of FIG. 2A, the transamination products 470A from transamination reactor 450A are fed into secondary ammonia recovery unit 372A. Secondary ammonia recovery unit 372A provides additional ammonia recovery capacity for process 300A. After ammonia recovery, the product stream 374A is then fed into primary ammonia/hydrogen recovery unit 350A for further processing. Stream 374A is a depiction of the ability to transfer materials between ammonia recovery units 350A and 372A. Due to the number of possible equipment combinations, 374A may actually be multiple flows passing between the two systems.

Figure 2B:
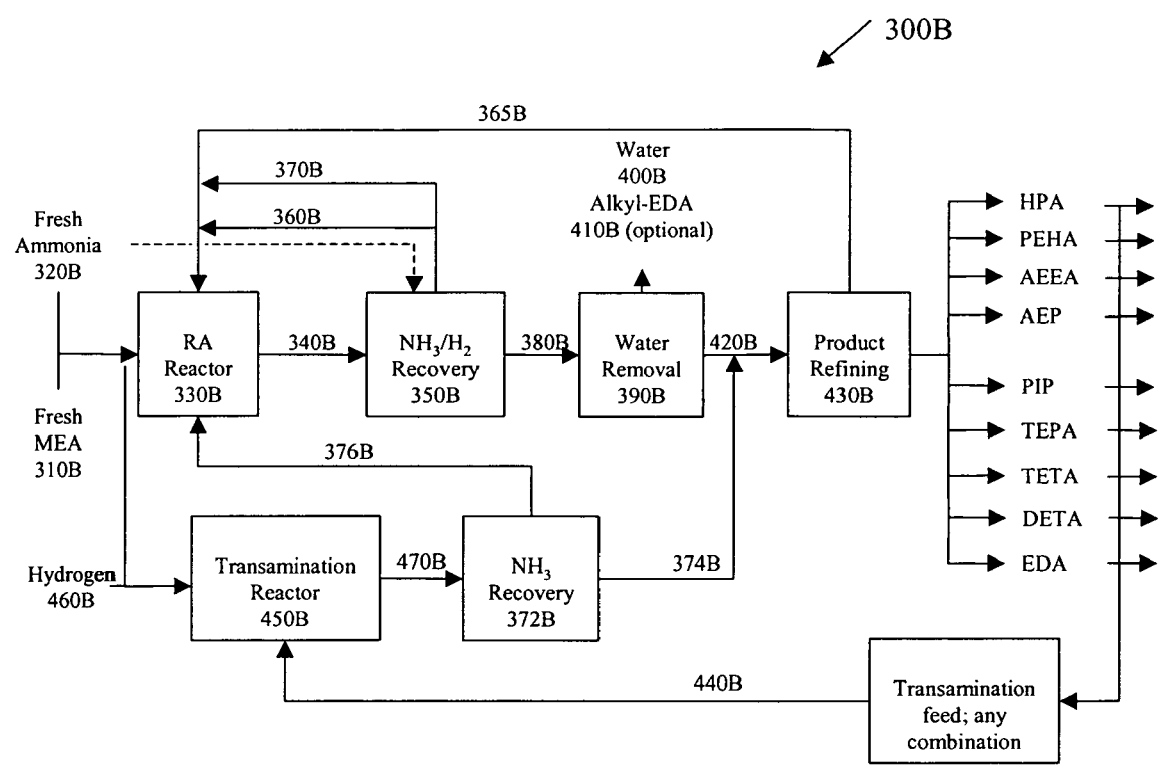
FIG. 2B is a flow chart of an embodiment of an ethyleneamines manufacturing process in accordance with the present invention.

Referring now to FIG. 2B, a process flow chart of an embodiment of a process of the invention using RA is shown. The process shown in FIG. 2B is representative of a partially-integrated process. Process 300B may be useful for adapting an existing RA line to make use of the process of the present invention. Process 300B includes primary ammonia/hydrogen recovery unit 350B and secondary ammonia recovery unit 372B. In the process of FIG. 2B, the transamination products 470B from transamination reactor 450B are fed into secondary ammonia recovery unit 372B. Secondary ammonia recovery unit 372B provides additional ammonia recovery capacity for process 300B. After ammonia recovery, the product stream 374B is then fed back into product stream 420B after water removal process 390B. Recovered ammonia 376B is recycled back into RA reactor 330B.

Figure 2C:
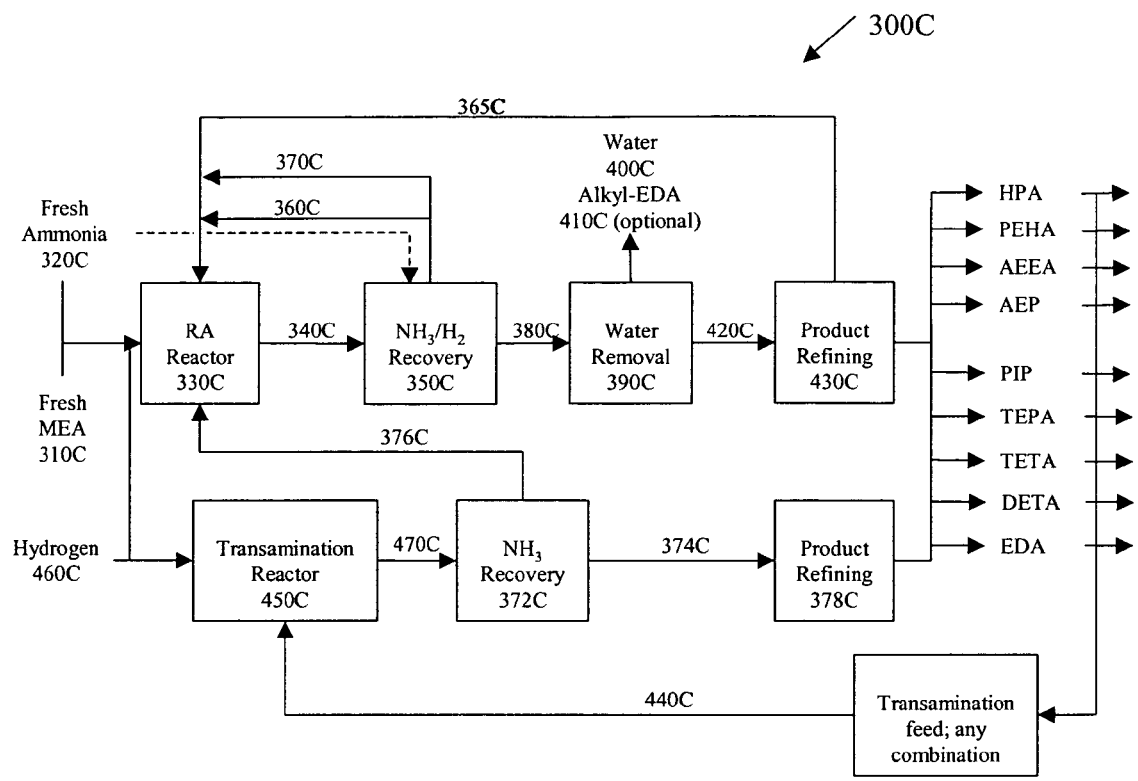
FIG. 2C is a flow chart of an embodiment of an ethyleneamines manufacturing process in accordance with the present invention.

Referring now to FIG. 2C, a process flow chart of an embodiment of a process of the invention using RA is shown. The process shown in FIG. 2C is representative of a partially-integrated process. Process 300C may be useful for adapting an existing RA line to perform the process of the present invention. Process 300C includes separate ammonia recovery and product refining streams for the RA reactor 330C and transamination reactor 450C. As shown in FIG. 2C, the product 470C of transamination reactor 450C is fed into ammonia recovery unit 372C. The product stream 374C from the ammonia recovery unit 372C is then fed into product refining unit 378C. The recovered ammonia 376C is recycled back into RA reactor 330C. The product refining unit 378C may be the same or different than product refining unit 430C that is used to treat the RA stream 420C.

Figure 2D:
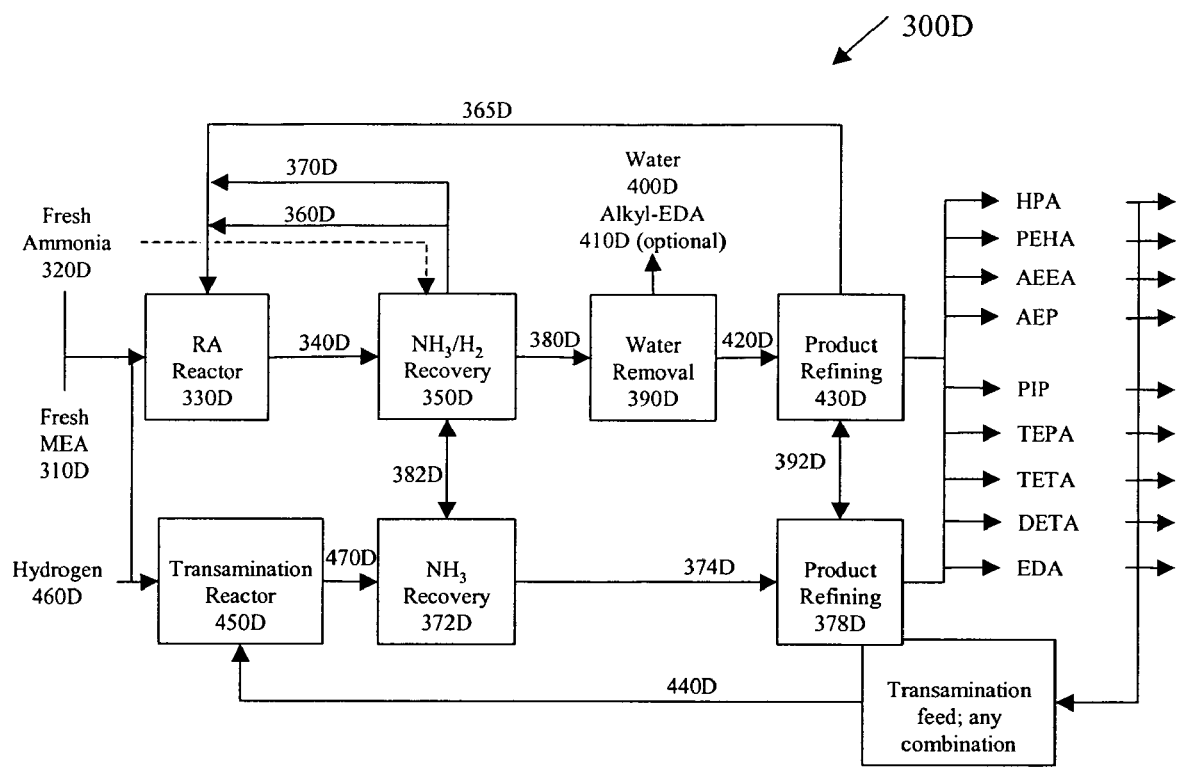
FIG. 2D is a flow chart of an embodiment of an ethyleneamines manufacturing process in accordance with the present invention.

Referring now to FIG. 2D, a process flow chart of an embodiment of a process of the invention using RA is shown. The process shown in FIG. 2D is representative of a partially-integrated process. Process 300D may be useful for adapting an existing RA line to perform the process of the present invention. Process 300D includes fully or partially-integrated ammonia recovery and product refining streams for the RA reactor 330D and transamination reactor 450D. As shown in FIG. 2D, the product 470D of transamination reactor 450D is fed into ammonia recovery unit 372D. The product stream 374D from the ammonia recovery unit 372D is then fed into product refining unit 378D. As shown in FIG. 2D, ammonia recovery units 350D and 372D are coupled by stream 382D. In similar fashion, product refining system 430D and 378D are coupled by stream 392D. This allows product from RA reactor 330D or transamination reactor 450D to be directed into the other stream for processing. It should be noted that streams 382D and 392D are a depiction of the ability to transfer materials between systems. Due to the number of possible equipment combinations 382D and 392D may actually be multiple flows going between the two systems.

The invention will now be described with reference to the following non-limiting examples.

EXAMPLES

Example 1

A process apparatus as shown in FIG. 1 was used to generate the following data. Operating conditions within the EDC Reactor were set to obtain approximately 49.6 wt. % EDA, 1.9 wt. % PIP, 24.3 wt. % DETA, 2 wt. % AEP, 21 wt. % heavies, and 1.2 wt. % other amine compounds. This composition was fed to a fixed bed reactor pressure of 800 psig and heated to a temperature of 145-155° C. 0.0003 wt. % hydrogen was then added to maintain catalyst activity. The mixture was fed to a transamination reactor containing a heterogeneous Ni—Re (6.8:1.8 wt. %) catalyst on a ⅟₁₆" alumina silica (80/20) support. Catalysts of this type are described in U.S. Provisional Patent Application having Ser. No. 61/195,455 and entitled "CATALYST COMPOSITIONS INCLUDING MIXED METAL OXIDE COMPLEX AS SUPPORT", filed Oct. 6, 2008 in the names of King et. al. The transamination reactor outlet was then combined with the EDC reactor outlet and sent to a shared refining system. TABLE 1-1 shows the product mix in weight % obtained at various temperatures.

TABLE 1-1

| | Feed (wt. %) | 145.2 (wt. %) | 145.1 (wt. %) | 150.4 (wt. %) | 150.5 (wt. %) | 155.8 (wt. %) | 155.3 (wt. %) | 144.9 (wt. %) |
|---|---|---|---|---|---|---|---|---|
| | | | | Temperature (° C.) | | | | |
| EDA | 49.6 | 37.3 | 37.3 | 32.0 | 31.9 | 25.6 | 25.5 | 34.8 |
| methyl EDA | 0.0035 | 0.0062 | 0.0063 | 0.0046 | 0.0061 | 0.0066 | 0.0076 | 0.0063 |
| ethyl EDA | 0.0029 | 0.0158 | 0.0156 | 0.0165 | 0.0153 | 0.0183 | 0.0195 | 0.016 |
| PIP | 1.9 | 4.9 | 4.9 | 7.4 | 7.4 | 11.5 | 11.5 | 4.7 |
| DETA | 24.3 | 25.4 | 25.4 | 24.9 | 24.9 | 22.6 | 22.6 | 23.7 |
| methyl DETA | 0.0052 | 0.0103 | 0.0046 | 0 | 0.0102 | 0 | 0 | 0.0051 |
| ethyl DETA | 0.0076 | 0.0179 | 0.0173 | 0.019 | 0.0192 | 0.0212 | 0.0219 | 0.0166 |
| AEP | 2.0 | 3.7 | 3.7 | 4.4 | 4.4 | 5.8 | 5.8 | 3.4 |
| MW 127 | 0.0364 | 0.0186 | 0.0185 | 0.0262 | 0.0259 | 0.0389 | 0.0381 | 0.02 |
| TETA's | 18.3 | 21.1 | 21.1 | 21.8 | 21.9 | 22.4 | 22.3 | 20.3 |
| TEPA's | 2.7 | 5.6 | 5.6 | 6.7 | 6.7 | 8.3 | 8.4 | 7.2 |
| Other amines | 1.1 | 2.0 | 2.0 | 2.6 | 2.6 | 3.7 | 3.9 | 5.8 |

TABLE 1-2

| | EDC Process (wt. %) | EDC + TA (wt. %) | EDC Process (wt. %) | EDC + TA (wt. %) |
|---|---|---|---|---|
| EDA | 37.1 | 37.3 | 34.3 | 34.8 |
| Crude PIP | 4.1 | 4.9 | 4.4 | 4.7 |
| DETA | 23.4 | 25.4 | 24.3 | 23.7 |
| AEP | 4.2 | 3.7 | 4.7 | 3.4 |
| TETA | 14.1 | 21.1 | 14.6 | 20.3 |
| TEPA | 6.8 | 5.6 | 7.1 | 7.2 |
| Other amines | 10.3 | 2.1 | 10.6 | 5.8 |

TABLE 1-2 provides a comparison at roughly equivalent amounts of EDA in the product mix. The product mix produced by an EDC process only affords much higher levels of the higher amines $\geq$N5 (which typically have less value than TETA) as compared to the EDC/TA integrated process. Levels of cyclics (AEP+PIP) and DETA are similar.

Example 2

A process apparatus as shown in FIG. 2 was used to generate the following data. Operating conditions within the RA Reactor were set to obtain approximately 32.5 wt. % EDA, 57.6 wt. % MEA, 1.5 wt. % PIP, 4.3 wt. % DETA, 3.8 wt % AEEA, and 0.3 wt. % others. This composition was fed to a fixed bed reactor pressure of 800 psig and heated to a temperature of 140-150° C. 0.0003 wt % hydrogen was then added to maintain catalyst activity. The mixture was then fed to a transamination reactor containing the catalyst described in Example 1. The transamination reactor outlet was then combined with the RA reactor outlet and sent to a shared refining system. TABLE 2-1 shows the product mix obtained at various temperatures.

TABLE 2-1

| | | Temperature (° C.) | |
|---|---|---|---|
| | Feed (wt. %) | 140 (wt. %) | 150 (wt. %) |
| EDA | 32.5 | 28.1 | 20.5 |
| methyl EDA | 0.0048 | 0.0148 | 0.0201 |
| MEA | 57.6 | 52.3 | 45.3 |
| ethyl EDA | 0 | 0.0085 | 0.0209 |
| PIP | 1.5 | 2.1 | 3.9 |
| DETA | 4.4 | 8.8 | 13.0 |

TABLE 2-1-continued

|  | Feed (wt. %) | Temperature (° C.) | |
|---|---|---|---|
|  |  | 140 (wt. %) | 150 (wt. %) |
| AEEA | 3.8 | 7.1 | 10.8 |
| DEA | 0 | 0 | 0.3 |
| AEP | 0.037 | 0.2 | 0.6 |
| HEP | 0.0121 | 0.0192 | 0.1 |
| TAEA | 0 | 0 | 0.0004 |
| TETA | 0 | 0.8 | 2.5 |
| TEPA | 0 | 0.2 | 0.5 |
| Other Amines | 0.2 | 0.4 | 2.4 |

TABLE 2-2

|  | RA + TA | RA Process | RA + TA | RA + TA | RA Process |
|---|---|---|---|---|---|
| EDA | 28.1 | 36.3 | 23.0 | 20.5 | 39.1 |
| MEA | 52.3 | 48.6 | 48.3 | 45.3 | 43.4 |
| PIP | 2.1 | 2.8 | 3.2 | 3.9 | 3.8 |
| DETA | 8.8 | 6.0 | 11.5 | 13.0 | 6.8 |
| AEEA | 7.1 | 4.5 | 9.4 | 10.8 | 4.7 |
| TETA | 0.8 | 0.6 | 1.8 | 2.5 | 0.8 |
| Other Amines | 0.9 | 1.1 | 2.7 | 4.0 | 1.4 |

TABLE 3-1

|  |  | Temperature (° C.) | | |
|---|---|---|---|---|
| Species | Feed | 140 | 150 | 160 |
| EDA | 33.7 | 27.9 | 22.8 | 15.8 |
| methyl EDA | 0.0097 | 0.013 | 0.017 | 0.0334 |
| MEA | 62.4 | 55.6 | 50.7 | 42.1 |
| ethyl EDA | 0.0058 | 0.0158 | 0.0225 | 0.0425 |
| PIP | 0.6 | 1.1 | 2.2 | 5.6 |
| DETA | 1.8 | 7.9 | 11.1 | 13.3 |
| AEEA | 1.5 | 5.6 | 8.5 | 12.1 |
| DEA | 0 | 0.0002 | 0.3 | 0.9 |
| AEP | 0.03 | 0.2 | 0.3 | 0.9 |
| HEP | 0.0014 | 0.0136 | 0.0703 | 0.4 |
| TAEA | 0 | 0 | 0.0002 | 0.0003 |
| TETA | 0 | 0.9 | 1.9 | 3.7 |
| TEPA | 0 | 0.2 | 0.4 | 0.9 |
| Other Amines | 0.012 | 0.5 | 1.6 | 4.4 |

TABLE 3-2

|  | RA + TA (wt. %) | RA Process (wt. %) | RA + TA (wt. %) | RA Process (wt. %) | RA + TA (wt. %) | RA Process (wt. %) |
|---|---|---|---|---|---|---|
| EDA | 27.9 | 33.3 | 22.8 | 36.3 | 15.8 | 40.4 |
| MEA | 55.6 | 55.1 | 50.7 | 48.6 | 42.1 | 41.7 |
| PIP | 1.1 | 1.8 | 2.2 | 2.8 | 5.6 | 4.0 |
| DETA | 7.9 | 4.7 | 11.1 | 6.0 | 13.3 | 7.3 |
| AEEA | 5.6 | 4.0 | 8.5 | 4.5 | 12.1 | 4.6 |
| TETA | 0.9 | 0.5 | 1.9 | 0.6 | 3.7 | 0.8 |
| Other Amines | 0.1 | 0.7 | 0.5 | 1.1 | 0.9 | 1.3 |

As TABLE 2-2 shows, comparing product mixes at roughly equivalent amounts of MEA in the product mix shows that the mix produced by a reductive amination (RA) process only affords much higher levels of EDA compared to the integrated RA/TA process. The RA/TA integrated process affords much higher levels of the desired DETA while maintaining low levels of PIP.

Example 3

A process apparatus as shown in FIG. 2 was used to generate the following data. Operating conditions within the RA Reactor are set to obtain approximately 33.7 wt. % EDA, 62.4 wt. % MEA, 0.6 wt. % PIP, 1.8 wt. % DETA, 1.5 wt. % AEEA, and 0.3 wt. % others. This composition was fed to a fixed bed reactor pressure of 800 psig and heated to a temperature of 140-160° C. 0.0003 wt % hydrogen was then added to maintain catalyst activity. The mixture was then fed to a transamination reactor containing the catalyst described in Example 1. The transamination reactor outlet is then combined with the RA reactor outlet and sent to a shared refining system. TABLE 3-1 shows the product mix obtained at various temperatures.

TABLE 3-2 gives a comparison, at roughly equivalent amounts of MEA in the product mix. The RA/TA integrated process affords much higher levels of the desired DETA and TETA while maintaining low levels of PIP compared to the reductive amination process.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention.

What is claimed is:

1. A method of manufacturing ethyleneamines, the method comprising the steps of:
   (a) manufacturing an ethyleneamines composition comprising a mixture of ethyleneamines using an ethyleneamine-generating process; and
   (b) transaminating at least a portion of the ethyleneamines composition in the presence of a hydrogenation/dehydrogenation catalyst to form a transaminated ethyleneamines composition;
   wherein the transaminated ethyleneamines composition comprises at least one ethyleneamine that is present in an amount that is greater than an amount that the at least one ethyleneamine is present in the ethyleneamines composition that is transaminated in step (b).

2. The method of claim 1, wherein the method further comprises the step of: removing at least a portion of at least one ethyleneamine from the ethyleneamines composition.

3. The method of claim 1, wherein the ethyleneamine-generating process comprises an ethylenedichloride (EDC) process.

4. The method of claim 1, wherein the ethyleneamine-generating process comprises a reductive amination (RA) process.

5. The method of claim 1, wherein the ethyleneamine-generating process comprises a condensation process.

6. A method of manufacturing ethyleneamines, the method comprising the steps of:
   (a) manufacturing an ethyleneamines composition comprising one or more ethyleneamines using an ethyleneamine-generating process selected from an ethylenedichloride (EDC) process, a reductive amination (RA) process, and a condensation process; and
   (b) transaminating at least a portion of the ethyleneamines composition in the presence of a transamination catalyst to form a transaminated ethyleneamines composition;
   wherein the transaminated ethyleneamines composition comprises at least one ethyleneamine that is present in an amount that is greater than an amount that the at least one ethyleneamine is present in the ethyleneamines composition that is transaminated in step (b).

7. The method of claim 1, wherein the ethyleneamines composition comprises any combination of two or more ethyleneamines selected from HPA, PEHA, AEEA, AEP, PIP, TEPA, TETA, DETA, and EDA.

8. The method of claim 1, wherein the transamination step increases the amount of at least one of TETA; DETA; EDA; or AEP that is present in the transaminated ethyleneamines composition as compared to the ethyleneamines composition that is transaminated in step (b).

9. The method of claim 1, wherein the transamination is conducted using a fixed bed reactor.

10. The method of claim 1, wherein the transamination is conducted over a transamination catalyst.

11. The method of claim 10, wherein the transamination catalyst comprising Ni, Cu, Co, Ru, Re, Rh, Pt, Pd, or a mixture thereof.

12. The method of claim 10, wherein the transamination catalyst comprises transitional alumina containing silica.

13. The method of claim 10, wherein the transamination catalyst comprises Re and Ni supported on an extruded $Al_2O_3$—$SiO_2$ support.

14. The method of claim 10, wherein the transamination catalyst comprises:
   (a) a support portion comprising an acidic mixed metal oxide comprising a transitional alumina and a second metal oxide; and
   (b) a catalyst portion comprising nickel and rhenium, wherein:
   the second metal oxide has a weight percentage that is less than the weight percentage of alumina,
   the catalyst portion is 25 weight percent or less of the catalyst composition,
   the catalyst portion comprises nickel in an amount in the range of 2 to 20 weight percent, based upon total catalyst composition weight, and
   there is no boron in the catalyst portion.

15. The method of claim 10, wherein the transamination catalyst comprises:
   (a) a support portion comprising an acidic mixed metal oxide comprising a transitional alumina and a second metal oxide, wherein the second metal oxide has a weight percentage that is less than the weight percentage of alumina; and
   (b) a catalyst portion comprising one or more metals selected from the group consisting of cobalt, nickel, and copper,
   wherein there is no, or less than 0.01 wt. % rhenium in the catalyst composition, and the catalyst portion is 25 wt. % or less of the catalyst composition.

16. The method of claim 15, wherein the catalyst portion comprises two or three metals selected from the group consisting of cobalt, nickel, and copper.

17. The method of claim 1, wherein the transamination is conducted in the presence of hydrogen.

18. The method of claim 1, wherein the transamination is conducted in the presence of ammonia.

19. The method of claim 1, wherein the transamination process is partially-integrated into the ethyleneamine-generating process.

20. The method of claim 1, wherein the transamination process is fully-integrated into the ethyleneamine-generating process.

* * * * *